United States Patent [19]

Machida

[11] 4,411,257
[45] Oct. 25, 1983

[54] INSPECTION ENDOSCOPE

[75] Inventor: Masashi Machida, Tokyo, Japan

[73] Assignee: Machida Endoscope Co., Ltd., Tokyo, Japan

[21] Appl. No.: 327,130

[22] Filed: Dec. 3, 1981

[30] Foreign Application Priority Data

Dec. 9, 1980 [JP] Japan .................... 55-175618

[51] Int. Cl.$^3$ ............................................ A61B 1/06
[52] U.S. Cl. ............................................ 128/6
[58] Field of Search .................. 128/4, 6, 21-23, 128/636, 665; 356/243, 256, 46

[56] References Cited

U.S. PATENT DOCUMENTS

| | | | |
|---|---|---|---|
| 2,050,608 | 8/1936 | Hellige | 456/243 |
| 3,520,626 | 7/1970 | Hach | 356/243 |
| 3,611,806 | 10/1971 | Hishikari | 356/46 |
| 3,730,632 | 5/1973 | Chikama | 128/6 |
| 3,773,425 | 11/1973 | Bentley | 356/243 |
| 3,799,668 | 3/1974 | McVeigh | 356/243 |
| 3,817,631 | 6/1974 | Kawahara | 128/6 |
| 4,259,020 | 3/1981 | Babb | 356/243 |

Primary Examiner—Kyle L. Howell
Assistant Examiner—Max F. Hindenburg
Attorney, Agent, or Firm—Berger & Palmer

[57] ABSTRACT

Disclosed is an inspection endoscope for medical or industrial applications, by which an observer can know the degree of the color change, inner pressure and temperature while the observer inspects, for example, the interior of the colon. In the eye lens zone of this inspection endoscope, not only the image of the inspection object fed from an image guide but also other factors such as the color, inner pressure and temperature are simultaneously displayed, and therefore, the inspection can be accomplished objectively while the inspection object is observed.

4 Claims, 5 Drawing Figures

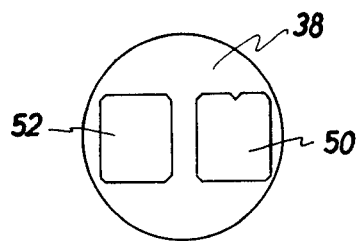
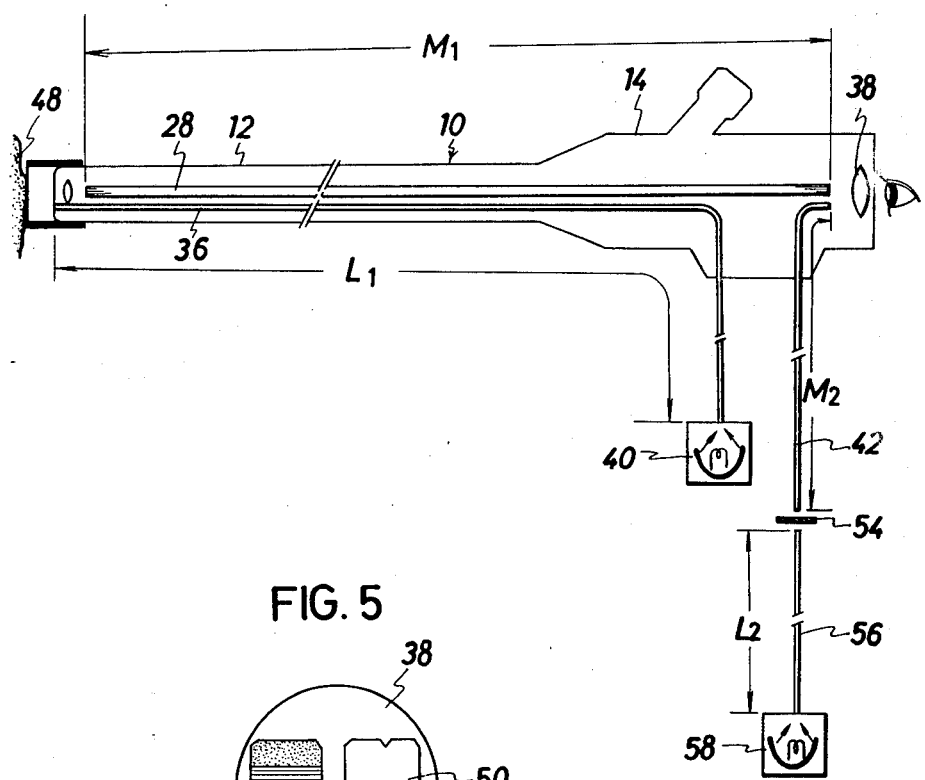
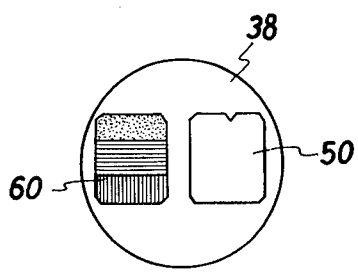

… (1)

INSPECTION ENDOSCOPE

BACKGROUND OF THE INVENTION (1) Field of the Invention

The present invention relates to an endoscope for use in observation or inspection. More specifically, the present invention relates to an inspection endoscope in which the image of the inspection object and other displays are simultaneously shown on the eye lens zone.

(2) Description of the Prior Art

A conventional medical or industrial endoscope has ordinarily the following structure and functions. By way of example, a conventional medical endoscope will now be described with reference to FIG. 1. As shown in FIG. 1, an endoscope 10 comprises a flexible tube 12 and a handle 14 contiguous thereto. An observation window 16, an air/water feed inlet 18, a suction opening 20, a forceps-projection opening 22 and an illuminating window 24 are formed on the top end of the flexible tube 12. One end of an image guide 28 composed of an optical fiber bundle confronts the observation window 16 through an object lens, and one end of an air/water feed tube 30 is connected to the air/water feed inlet 18. One end of a suction tube 32 is connectd to the suction opening 20 and one end of a forceps guide tube 34 is connected to the forceps-projecting opening 22. One end of a light guide 36 composed of an optical fiber bundle is connected to the illuminating window 24. The other end of the image guide 28 confronts an eye lens zone 38 of the handle 14, and the air/water feed tube 30 is extended beyond the handle 14 and branched in the end portion (not shown) and the respective ends are connected to air and water feed pumps. Also the suction tube 32 is extended beyond the handle 14 and the other end is connected to a suction pipe (not shown). The light guide 36 is extended beyond the handle 14 and the other end confronts a light source 40 such as a xenon lamp. The other end of the forceps guide tube 34 is opened to the top face of the handle 14.

When the interior of the colon is observed by the conventional endoscope having the above-mentioned structure, the flexible tube 12 is inserted into the colon and a polyp or ulcer is observed by the image guide 28 through the light emitted from the light guide, and if necessary, the polyp or the like is picked up by the forceps to collect a specimen or perform a medical treatment.

When the interior of the colon is thus observed, the degree of the color change in the ulcer or the like is judged with reference to a color chart and the size of the polyp is judged based on the size displayed in the eye lens zone. Furthermore, the observation is conducted while checking data of the blood pressure and pulse displayed on a tonometer and a pulsimeter.

When the observation is carried out in the foregoing manner, data on the tonometer or pulsimeter is read by the observer removing his the eyes from the eye lens zone. Accordingly, the conventional endoscope is defective in that the observation is interrupted when data on the tonometer or pulsimeter is checked.

Furthermore, when the degree of the color change is judged with reference to the color chart, since optical fibers constituting the image guide have an inherent light decay characteristic, the properties of the color are changed according to the length of the image guide. Accordingly, in the actual operation, even if the color of the affected part is the same as a certain color of the color chart, the observed color is different from the actual color since the color is changed according to the length of the image guide. Therefore, the conventional endoscope also is defective in that accurate inspection or correct diagnosis cannot be made.

SUMMARY OF THE INVENTION

According to the present invention, the end of an image guide and the ends of other data introduction guides for transmitting data are arranged in parallel opposite an eye lens zone, and such data as the color of a color chart, the inner pressure, the inner temperature and the size are transmitted to the eye lens zone through data introduction guides.

It is therefore a primary object of the present invention to provide an endoscope in which an image of an inspection object and desired data are simultaneously displayed on the eye lens zone to enable checking of the necessary data while continuing the observation, whereby accurate and objective observation can be performed.

Another object of the present invention is to provide an endoscope in which in judging the degree of the color change of the objective part by comparing the color of the objective part with a color chart, the condition for transmitting the color of the color chart to the eye lens zone is made identical with the condition for transmitting the image of the objective part by an image guide by applying a light to the objective part by a light guide to uniformalize the light decay condition among optical fibers, whereby the color of the objective part is compared with the color of the color chart under the same condition to enable accurate obervation.

These and other objects and features of the present invention will become apparent from the following detailed description with reference to the accompanying drawings which are given only for illustration but by no means limit the scope of the invention.

BRIEF DESCRIPTION OF THE DRAWINGS

FIG. 3 is a plan view showing the display state of an observation object and data transmitted to an eye lens zone.

FIG. 4 is a sectional side view showing another embodiment of the endoscope according to the present invention.

FIG. 5 is a plan view showing the state of an eye lens zone when a color identifying sheet is used as the data.

DETAILED DESCRIPTION OF THE PREFERRED EMBODIMENTS

Figure 1:
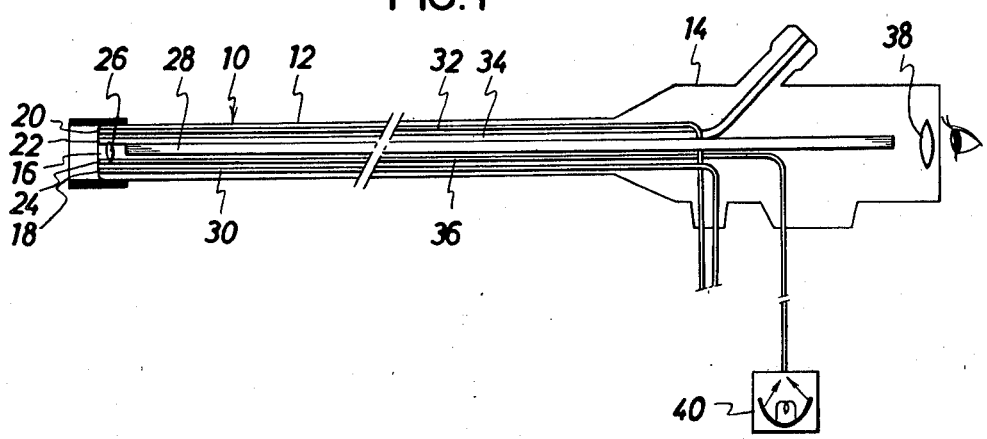
FIG. 1 is a sectional side view illustrating a conventional endoscope.
Figure 2:
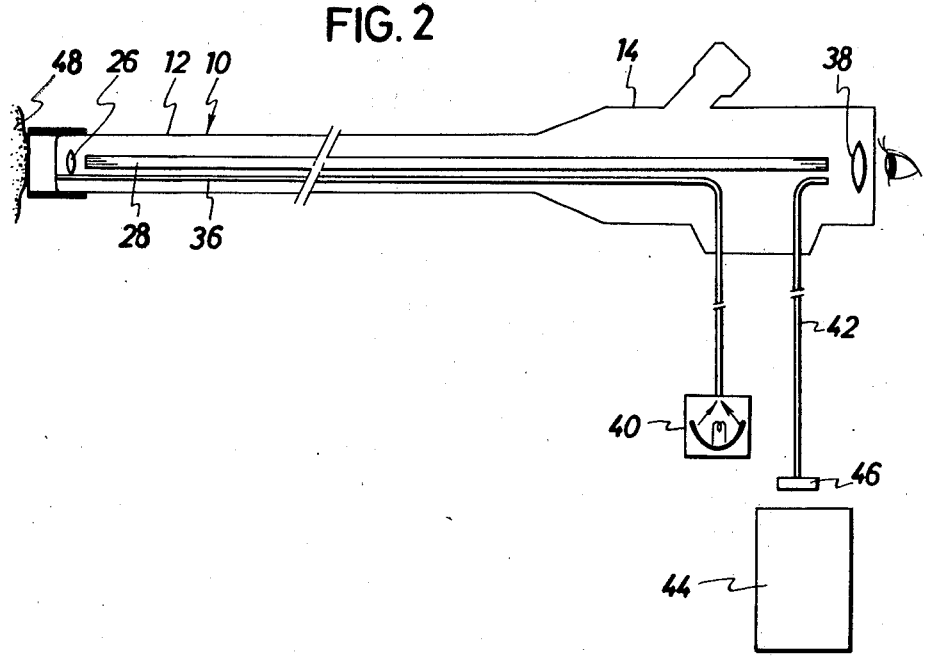
FIG. 2 is a sectional side view showing one embodiment of the endoscope of the present invention.

FIG. 2 illustrates one embodiment of the endoscope of the present invention. Referring to FIG. 2, an endoscope 10 comprises a flexible tube 12 and a handle 14 contiguous thereto. One end of an illuminating light guide 36 composed of an optical fiber bundle is located at the position of the top end of the flexible tube 12, and a light is emitted from an illuminating window formed on the top end of the light guide 36 to effect illumination. The other end of the light guide 36 is opposite an illuminating light source 40 such as a xenon lamp 40. One end of an image guide 28 composed of an optical fiber bundle is opposite an observation window through an object lens and the other end of the image guide 28 is opposite an eye lens zone 38 of the handle 14. A data introduction guide 42 is prepared in the same manner as the image guide 28, and one end of the data introduction guide 42 is opposite the eye lens zone 38. An attachment 46 is attached to the other end of the data introduction guide 42 so that said other end is opposite a data device 44 such as a pressure gauge, a scale or a thermometer.

In the foregoing description and drawings, the forceps guide tube, air/water feed tube and suction pipe described hereinbefore with respect to the conventional endoscope are omitted because they are not directly relevant to the present invention. These members may be disposed according to need and other necessary members may optionally be attached to the endoscope according to the intended use.

In the endoscope 10 having the above-mentioned structure, the end portion of the data introduction guide 42 is connected to a desirable data device 44, and the flexible tube 12 is inserted into, for example, an observation part in the colon. The light of the light source 40 is applied to the observation part through the light guide 36 and an image 50 of an observation object 48 is transmitted to the eye lens zone 38 through the image guide 28. Simultaneously, data 52 is transmitted to the eye lens zone 38 from the data device 44. As shown in FIG. 3, the image 50 of the observation object 48 and the data 52 are simultaneously displayed on the eye lens zone 38. Thus, an observer can examine the observation object while reading the necessary data 52.

As the necessary data, in case of a medical endoscope, there can be mentioned, for example, the blood pressure, the pulse number, the scale and the inner pressure of the colon, and in case of an industrial endoscope, there can be mentioned, for example, the pressure, the temperature, the pH value and the scale. Of course, a plurality of necessary data may simultaneously be transmitted to the eye lens zone.

As will be apparent from the foregoing description, according to the present invention having the above-mentioned structure and function, the observation object and necessary data can simultaneously be transmitted to the eye lens, and an observer can judge the observation object objectively based on necessary data.

FIG. 4 illustrates another embodiment of the endoscope according to the present invention. In FIG. 4, reference numerals 36, 40, 28, 38 and 54 represent an illuminating light guide, an illuminating light source, an image guide, and an eye lens zone, respectively. A color identifying sheet 54, light guide 56, and light source 58 constitute the data device. The light guide and 56 for illuminating the color identifying sheet 54 is composed of an optical fiber bundle and one end of the light guide 56 is opposite the light source 58 having the same light quantity as that of the illuminating light source 40 while the other end of the light guide 56 is opposite the color identifying sheet 54. One end of a data introduction guide 42 is opposite the eye lens zone 38 and the other end of the data introduction guide 42 is opposite the color identifying sheet 54.

The color identifying sheet 54 comprises a color chart and a film and provides a color to be compared with the color of an observation object 48 to identify the color of the object 48. A plurality of colors may be provided according to need.

In the above-mentioned structure, in order to eliminate the difference of the color transmitting and reproducing characteristics owing to the decay characteristics of optical fibers, the length L1 of the light guide 36 is made equal to the length L2 of the light guide 56 for illuminating the color identifying sheet and the length M1 of the image guide 28 is made equal to the length M2 of the data introduction guide 42. Thus, the condition for illuminating the observation object 48 is made equal to the condition for illuminating the color identifying sheet 54 by the light guide 56, and the light decay condition of the image guide 28 from the observation object 48 to the eye lens zone 38 is made equal to the light decay condition of the data introduction guide 42 from the color identifying sheet 54 to the eye lens zone 38.

The operation of the endoscope of the above embodiment will now be described. The top end portion of the endoscope 10 is inserted into a position of the observation object 48 and caused to impinge against the observation object 48, and observation is then carried out. Since the length L1 is made equal to the length L2 and the length M1 is made equal to the length M2 as described above, the difference of the color transmitting characteristic in optical fibers is eliminated and the condition for illuminating the observation object 48 is made equal to the condition for illuminating the color identifying sheet. As shown in FIG. 5, therefore, in the field of a vision of the eye lens zone 38, the image 50 of the observation object 48 and the image 60 of the color identifying sheet 54 are observed under the same conditions. Accordingly, the image 50 of the observation object 48 can be examined according to the image 60 of the color identifying sheet 54 and the observation object 48 can be judged objectively and accurately.

In the foregoing embodiment, for example, in case of a medical endoscope, if an effected part in the colon, as the observation object, is dyed with a reagent, the degree of dyeing can accurately be compared with the color identifying sheet, and the state of the affected part can be judged correctly.

The foregoing description and drawings are given only for illustrating the fundamental embodiments of the present invention, and as is apparent to those skilled in the art, various omissions, substitutions and modifications may be made to these embodiments without departing from the scope of the present invention.

What is claimed is:

1. An inspection endoscope comprising an eyepiece, an insertion tube having an image guide and a first light guide extending therethrough with a first end of each located opposite an object to be observed, a handle portion including said eyepiece permitting visual observation of an object being observed, a first light source located opposite the second end of said first light guide to carry light to illuminate the object being observed, said eyepiece located at the second end of said image guide and an improvement comprising a data introduction guide having a first end opposite a data device and a second end located at said eyepiece, said data device comprising a display related to the observation being made, said display comprising data to be simultaneously visually compared while the object is being observed, said display comprising a color identifying sheet, said data device further comprising a second light source and a second light guide, a first end of said second light guide located opposite said second light source and a second end of said second light guide located opposite said color identifying sheet with the combination of said second light source, said second light guide and said data introduction guide presenting the same optical decay characteristics as the combination of said first light source, said first light guide and said image guide.

2. An inspection endoscope as set forth in claim 1, wherein said first and second light sources are of equal power.

3. An inspection endoscope as set forth in claim 2, wherein the length of said first light guide equals the length of said second light guide and the length of said data introduction guide equals the length of said image guide.

4. An inspection endoscope as set forth in claim 2, wherein the optical decay characteristics of said first and second light guides are equal as are those of said image guide and said data guide.

* * * * *